(12) United States Patent
Bratlie et al.

(10) Patent No.: US 10,722,259 B2
(45) Date of Patent: Jul. 28, 2020

(54) IMPLANT REMOVER

(71) Applicant: REMOVAID AS, Oslo (NO)

(72) Inventors: Marte Bratlie, Oslo (NO); Erik Tandberg Askevold, Oslo (NO); Erik Elwing, Jönköping (SE); Emma Widehäll, Taberg (SE); Anna Arlbrandt, Tenhult (SE); Fredrik Ejdehag, Vaggeryd (SE); Ronny Brakya, Jönköping (SE)

(73) Assignee: REMOVAID AS, Oslo (NO)

( * ) Notice: Subject to any disclaimer, the term of this patent is extended or adjusted under 35 U.S.C. 154(b) by 290 days.

(21) Appl. No.: 15/735,271

(22) PCT Filed: Jun. 7, 2016

(86) PCT No.: PCT/EP2016/062863
§ 371 (c)(1),
(2) Date: Dec. 11, 2017

(87) PCT Pub. No.: WO2016/198381
PCT Pub. Date: Dec. 15, 2016

(65) Prior Publication Data
US 2018/0168673 A1    Jun. 21, 2018

(30) Foreign Application Priority Data

Jun. 12, 2015  (GB) .................................. 1510260.1

(51) Int. Cl.
*A61B 17/30* (2006.01)
*A61B 17/3209* (2006.01)
(Continued)

(52) U.S. Cl.
CPC ............ *A61B 17/30* (2013.01); *A61B 17/285* (2013.01); *A61B 17/32093* (2013.01);
(Continued)

(58) Field of Classification Search
CPC ....... A61B 17/22; A61B 17/285; A61B 17/30; A61B 17/32; A61B 17/320016;
(Continued)

(56) References Cited

U.S. PATENT DOCUMENTS

2007/0276409 A1* 11/2007 Ortiz .................. A61B 17/0682
606/139
2008/0188877 A1   8/2008 Hickingbotham
(Continued)

FOREIGN PATENT DOCUMENTS

DE          27 13 386 A1    11/1978
DE      10 2009 009736 A1    8/2010

OTHER PUBLICATIONS

International Preliminary Report on Patentability dated Dec. 21, 2017 for corresponding International Patent Application No. PCT/EP2016/062863.
(Continued)

*Primary Examiner* — Robert A Lynch
(74) *Attorney, Agent, or Firm* — Tarolli, Sundheim, Covell & Tummino LLP

(57) ABSTRACT

Disclosed herein is a tool for removing an implanted item from beneath the skin, the tool comprising: a clamping device configured to engage with the skin to retain the implanted item in a known position relative to the tool; a cutting device for cutting an opening in the skin; and a gripping device configured to move through an opening in the skin and grip an implanted item; such that, in use, the implanted item is retained by the clamping device substantially in the known position and the cutting device creates an opening in the skin through which the gripping device then passes to grip an implanted item. Advantageously, the tool reduces the complexity of an implant removal process and does not require significant operator skill to use. It further (Continued)

reduces the time required and the variation in the outcome of such a procedure.

36 Claims, 13 Drawing Sheets

(51) Int. Cl.
    *A61B 17/285*     (2006.01)
    *A61B 17/50*     (2006.01)
    *A61B 17/32*     (2006.01)
    *A61B 17/00*     (2006.01)

(52) U.S. Cl.
    CPC .... *A61B 17/50* (2013.01); *A61B 2017/00353* (2013.01); *A61B 2017/00747* (2013.01); *A61B 2017/320064* (2013.01)

(58) Field of Classification Search
    CPC ............ A61B 17/3205; A61B 17/3209; A61B 17/32093; A61B 17/50; A61B 2017/00353; A61B 2017/306; A61B 2017/308; A61B 2017/505
See application file for complete search history.

(56) References Cited

U.S. PATENT DOCUMENTS

2009/0163943 A1    6/2009  Cavanaugh
2014/0163318 A1\*  6/2014  Swanstrom ........ A61B 17/3431
                                                                         600/104

OTHER PUBLICATIONS

International Search Report dated Jul. 7, 2016 for corresponding International Patent Application No. PCT/EP2016/062863.

\* cited by examiner

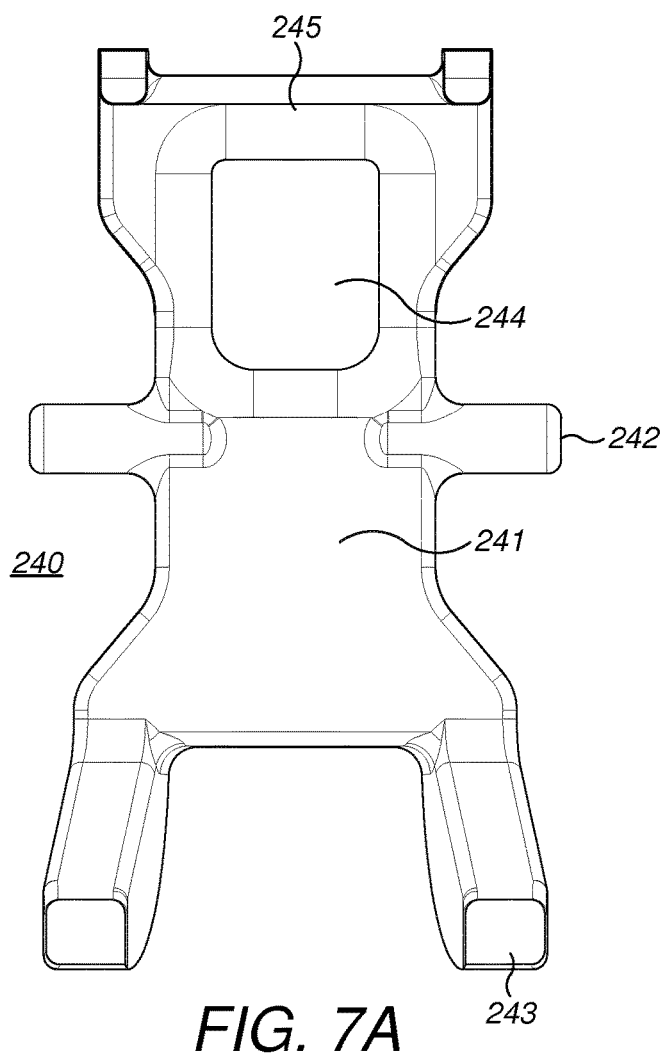
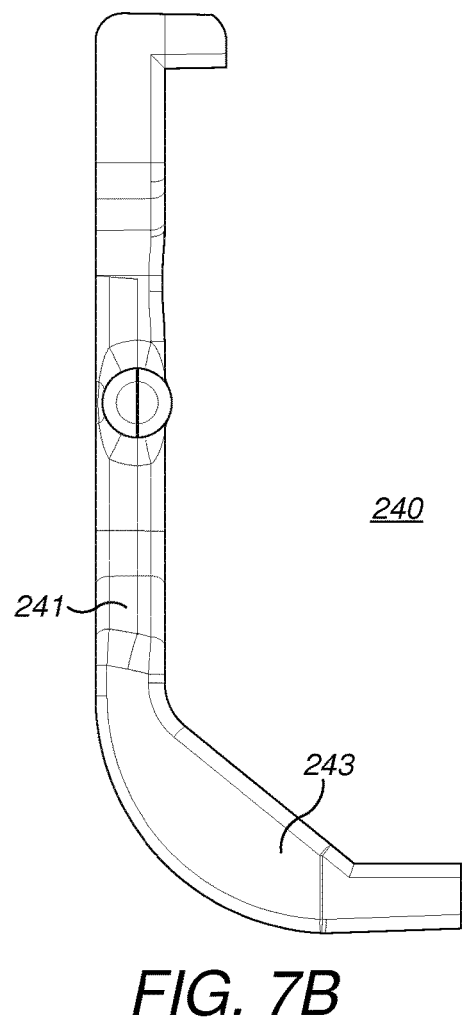
FIG. 7A
FIG. 7B

IMPLANT REMOVER

RELATED APPLICATIONS

The present application is a U.S. National Stage application under 35 USC 371 of PCT Application Serial No. PCT/EP2016/062863, filed on 7 Jun. 2016; which claims priority from GB Patent Application No. 1510260.1, filed 12 Jun. 2015, the entirety of both of which are incorporated herein by reference.

FIELD OF THE INVENTION

This invention relates to a tool for use in a surgical procedure. More particularly, embodiments provide a tool for removing an implant from a body.

BACKGROUND OF THE INVENTION

There is an increasing use of long-term contraceptives, of which one type is a subdermal implant in the form of a rod that releases contraceptive hormone, until it needs to be removed or replaced with a new rod. For example, Nexplanon [Schering-Plough Limited/Merck, Sharp & Dohme Limited (MSD) US] is a subdermal implant indicated for use as a long-term contraceptive for women. It entered the European market in 2010, replacing Implanon (available in Europe and SE Asia since 1998, and approved in the US in 2006), the most widely used implantation system in the world, marketed in 32 or more countries throughout the world. The implant of both Implanon and Nexplanon is a 4 cm long, 2 mm diameter non-biodegradable ethylene vinyl acetate (EVA) copolymer core, containing 68 mg of the synthetic progestin etonogestrel, surrounded by a rate-controlling EVA copolymer membrane. The implant must be replaced or removed 3 years after insertion.

Other contraceptive implants are Jadelle, 43 mm long, 2.5 mm diameter (2 rods), lasts 5 yrs, and Sino-Implant II, 44 mm long, 2.4 mm diameter (2 rods), lasts 4 yrs.

Increased focus on the benefits of long-acting, reversible contraception has spurred an increase in CI insertions in recent years, both in industrialised and developing countries. On a global scale, multiple campaigns have been launched to meet UN Millennium Goals 4 and 5, i.e. reduction of maternal and child mortality, and a steep increase in CI procurement is expected for the foreseeable future. A large and increasing number of women will therefore need to have their CIs removed.

Since CIs were introduced to the commercial market in the early 1980s, implant manufacturers have focused intense efforts on making insertion of CIs easier. For instance, a unique, preloaded disposable applicator developed for Nexplanon ensures "fail proof" and efficient subdermal insertion of the implant. CI removals, on the other hand, have largely been left untouched and at the mercy of the various service providers. The CI removal procedure recommendations have remained essentially unchanged for 40 years, relying on general surgical skills from the service provider.

While contraceptive implant (CI) insertion is easily managed through the use of specialised introducer trocars, CI removal is a complex task that requires specialist training. There exists no standardised method for CI removal, and no dedicated removal devices are available on the global market. Currently, CIs are removed using scalpels and forceps and rely on the general surgical skills of the service provider.

The currently accepted procedure generally involves a minimum of three essential steps. Firstly, the position of the CI beneath the skin is identified through palpation; secondly an incision of appropriate size must be made at a suitable position relative to the CI; the CI must then be relocated and extracted, typically by using forceps brought through the incision in the skin.

The complexity of the procedure means that it is highly variable in duration and often cumbersome, both for the patient and for the clinician. The complex current CI removal procedure is a major impediment to a desired increase of CI use.

Introducing a simple, safe and effective CI removal procedure could improve patient care, be cost-effective for CI service providers and increase access to complete CI care. All available research shows that the procedure length of the current CI removal procedure is highly variable and heavily reliant on individual operator skills.

More recently, in WO 2013/156628, devices have been described which allow for an implant to be held in a fixed, known position beneath the skin, thus facilitating a standardised approach to the removal procedure by offering a precise point of entry of a scalpel in relation to the implant lying beneath the skin. Such devices aid in reducing the complexity of the procedure by providing a simple method to achieve the first step of the procedure leaving the operator free to complete the remaining steps.

Although such devices make progress in reducing the complexity of the procedure, the remaining stages of making an incision in the skin and extracting the implant are those that require the most operator skill. The time required and the outcome quality of the finished procedure are therefore still highly variable.

Accordingly there exists a need for providing a means to remove a contraceptive implant from beneath the skin which reduces the complexity of the process such that it does not require a high level of operator skill, which also further reduces the time required to remove the implant and reduces the variation in the outcome of the procedure.

SUMMARY OF THE INVENTION

According to a first aspect of the present invention, there is provided a tool for removing an implanted item from beneath the skin, the tool comprising: a clamping device configured to engage with the skin to retain the implanted item in a known position relative to the tool; a cutting device for cutting an opening in the skin; and a gripping device configured to move through an opening in the skin and grip an implanted item; such that, in use, the implanted item is retained by the clamping device substantially in the known position and the cutting device creates an opening in the skin through which the gripping device passes to grip the implanted item Preferably the cutting device is configured to move between: a first position, in which the cutting device is retracted within the tool; and a second position in which the cutting device extends out of the tool; such that, in use, the movement of the cutting device to the second position brings the cutting device into contact with the skin and cuts an opening in the skin through which the gripping means can pass.

Preferably the tool further comprises a first actuating means configured to control the movement of the cutting device; such that, in use, when the first actuating means is activated by a user, the cutting device cuts an opening in the skin.

Preferably the actuating means comprises a first handle and is configured so that, in use, the pressing of the first handle by a user compresses a spring within the housing; and continued pressing of the first handle releases the compressed spring so as to cause the movement of the cutting device.

Preferably the maximum movement of the cutting device out of the tool is limited by a first stop to the second position.

Preferably the stop comprises a protrusion on the cutting device configured to contact an element of the tool such that further movement of the cutting device out of the tool is prevented.

Preferably the tool comprises a second protrusion on the cutting device, the protrusion configured to contact the implanted item such that, in use, cutting of the implanted item is substantially restricted.

Preferably the cutting device comprises one or more blades.

Preferably the cutting device comprises two or more blades, the blades integrally formed as a single unit.

Preferably the cutting device comprises two or more separate blades.

Preferably the cutting device comprises two substantially coplanar blades.

Preferably the lateral separation of the blades is configured such that, in use, parts of the blades enter the skin either side of the implanted item to produce two initial openings.

Preferably the coplanar blades have equally extending pointed tips and opposing angled cutting edges; wherein the blades are configured such that, in use, the tips enter the skin either side of the implanted item and continued motion of the blades into the skin results in the angled cutting edges extending the initial openings towards one another.

Preferably the opposing angled cutting edges meet centrally to form a continuous cutting edge.

Preferably the gripping device is configured to move between a first position and a second position, wherein the second position of the gripping device at least partially coincides with the second position of the cutting device, such that, in use, the gripping means moves through the opening in the skin cut by the cutting device.

Preferably the gripping device is configured to move independently to the cutting device.

Preferably the tool further comprises a second actuating means configured to control the movement of the gripping means, such that, in use, when a user activates the second actuating means, the gripping device moves to the second position of the gripping device, entering the opening in the skin cut by the cutting device and grips the implanted item.

Preferably the second actuating means comprises a second handle of the tool, the second handle being in mechanical communication with the gripping device such that movement of the second handle causes a corresponding movement of the gripping device.

Preferably the gripping device comprises a tweezer member, the tweezer member comprising opposing gripping arms configured to grip an implanted item.

Preferably the gripping device further comprises a mechanism configured to hold the opposing gripping arms together in a gripping position.

Preferably the mechanism holds the gripping arms together after the gripping device reaches the second position.

Preferably the gripping device and cutting device are the same unit.

Preferably the cutting device comprises one or more blades and the gripping device is provided by a notch in the one or more blades, the notch configured to grip the implanted item such that, movement of the cutting device into the skin, causes the one or more blades to firstly cut an opening in the skin and continued movement brings the notch through the opening into contact with the implant to grip it.

Preferably the cutting device comprises two or more opposing blades and the gripping device is provided by the gripping action of the two or more opposing blade jaws.

Preferably the clamping device comprises two or more opposing pinching surfaces configured to engage with the skin; wherein the separation between the surfaces may be varied.

Preferably the clamping device further comprises: a locking mechanism configured to releasably lock one or more of the pinching surfaces in position at a predetermined separation.

Preferably at least one of the pinching surfaces forms a wedge shape such that, when the surfaces are brought together in use, the wedge shaped surface moves at least partially below the implanted item to lift it and facilitate the improved retention of the implanted item.

Preferably the tool further comprises a housing for containing the cutting device and gripping device.

Preferably the housing comprises: a hollow body with an opening at a first end, wherein the cutting device and gripping device are configured to move relative to the housing such that they are wholly contained within the body of the housing when in their first positions and extend through the opening at the first end when in their second positions.

Preferably the clamping device is provided at the first end of the body of the housing, such that, in use, the clamping device engages with the skin and subsequent movement of the cutting device and gripping device to their second positions brings them through the opening in the housing into contact with the skin and the cutting device cuts an opening in the skin through which the gripping device grips the implanted item.

Preferably the housing is configured to act as a hand grip such that, in use, when the gripping device has gripped the implant, the user may pull the tool away from the skin to extract the implant through the opening in the skin.

Preferably the tool is configured to be used only once.

Preferably the cutting device and gripping device may be reset to their first positions after use such that the tool may be used multiple times.

Preferably parts of the tool are configured for multiple use and parts of the tool are configured for single use.

Preferably the tool further comprises a lighting device.

According to a second aspect of the invention there is provided a method for using a tool to remove an implanted item from beneath the skin comprising the steps of: operating a clamping device of the tool to retain an implanted item in a known position relative to the tool; operating a cutting device of the tool to cut an opening in the skin; and operating a gripping device of the tool to grip an implanted item through an opening in the skin.

Preferably the method further comprises the step of: releasing the clamping device and operating a hand grip of the tool to pull the tool away from the skin after operating the gripping device such that the implanted item is removed through an opening in the skin.

Preferably the tool used in the second aspect of the invention is the tool of the first aspect of the invention.

Embodiments of the present invention simplifies the removal process of an implanted item that is positioned/implanted under the skin (e.g. subdermally or subcutaneously), in particular a contraceptive implant such as those described above, or other pharmaceutical subdermal or subcutaneous implants. A tool according to embodiments of the invention aids the removal by providing the functionality to complete all of the steps of the CI removal procedure. Firstly the tool allows for fixing the position of the implant in a known position under the skin near where an incision is to be made; secondly, the tool allows for a controlled incision to be made of reproducible size and positioning at an appropriate location relative to the fixed implant; thirdly the tool provides a means to grip the implant by providing a gripping means which may be reliably extended through the incision in the skin; and finally the device allows for the implant to be removed through the incision.

The tool according to embodiments of the invention therefore allows for the regulation of the complete contraceptive implant extraction process, radically changing the conventional CI removal procedure. An advantage of use of this tool is that operation does not require any significant user skill, since the main steps are regulated by the features of the tool, yet the procedure has a high reproducibility and high finish quality. The size of incision is highly regulated and damage to the skin and surrounding tissue is minimised. The skill required in successfully finding the implant to directly grip it through the incision is completely removed, with this step in the process regulated by the functionality of the tool. Accordingly, the complete extraction process is standardised and the time taken to complete the procedure significantly reduced. This tool therefore has the potential to facilitate CI removal on a large scale whilst maintaining a high level of finish quality and therefore may aid in meeting the forecasted high global demand for CI removal related to the steep increase in CI procurement.

BRIEF DESCRIPTION OF DRAWINGS

Embodiments of the present invention will now be described, by way of example only, with reference to the accompanying drawings, in which:

FIGS. 7A and 7B show a front and side view of a movement regulator of the cutting device according to an embodiment;

DESCRIPTION OF EMBODIMENTS

Embodiments of the invention solve at least some of the above-identified problems by providing a single tool 100 comprising all of the means to perform each step required in a contraceptive implant extraction procedure. Since each step is provided by the functionality of the components of the tool, the variation in each step in significantly reduced, enhancing the reproducibility and speed at which the procedure is performed. Furthermore the tool does not require significant training to operate and therefore a contraceptive implant may be extracted without requiring the skill of a trained clinician.

A tool of the invention may be single use, i.e. disposable, or it may be capable of being used multiple times. An advantage of the tool being designed only for single use is that the tool can be distributed to a user in a sterilised package with all the parts of the tool sterilised. The terms "implant", "foreign body" and "implanted item" are used herein interchangeably. The foreign body that is positioned under the skin may be any medical subdermal or subcutaneous implant or e.g a microchip. Preferably it is a contraceptive implant. Preferably, it is elongate. Preferably, it is rod-shaped.

The tool comprises a cutting device configured for making the required incision in the skin to provide an opening through which the contraceptive implant may be extracted. The cutting device preferably includes one or more blades configured to produce an incision of appropriate shape, size and depth, such that the implant may be extracted without causing excessive damage to the skin, surrounding tissue or implant.

The tool also provides a gripping device for entering through the opening in the skin made by the cutting device and gripping the implant. The gripping device preferably comprises a tweezer member, configured to move through the opening in the skin and maintain a gripping position around the implant such that the tool may subsequently be pulled away from the skin to remove the implant.

The tool preferably includes a clamping device configured to hold the implant in place beneath the skin in a known position relative to the tool, thereby providing the initial step in the implant extraction process.

The tool preferably includes a housing of appropriate shape to provide a hand grip to a user such that, once the implant is clamped in place, the cutting device extended to make the incision and the implant gripped by the gripping means, the tool may be pulled away from the skin by the user to extract the gripped implant through the opening in the skin. The tool therefore may provide each step in the implant extraction process.

Overview of Tool Components and Arrangement

Figure 1:
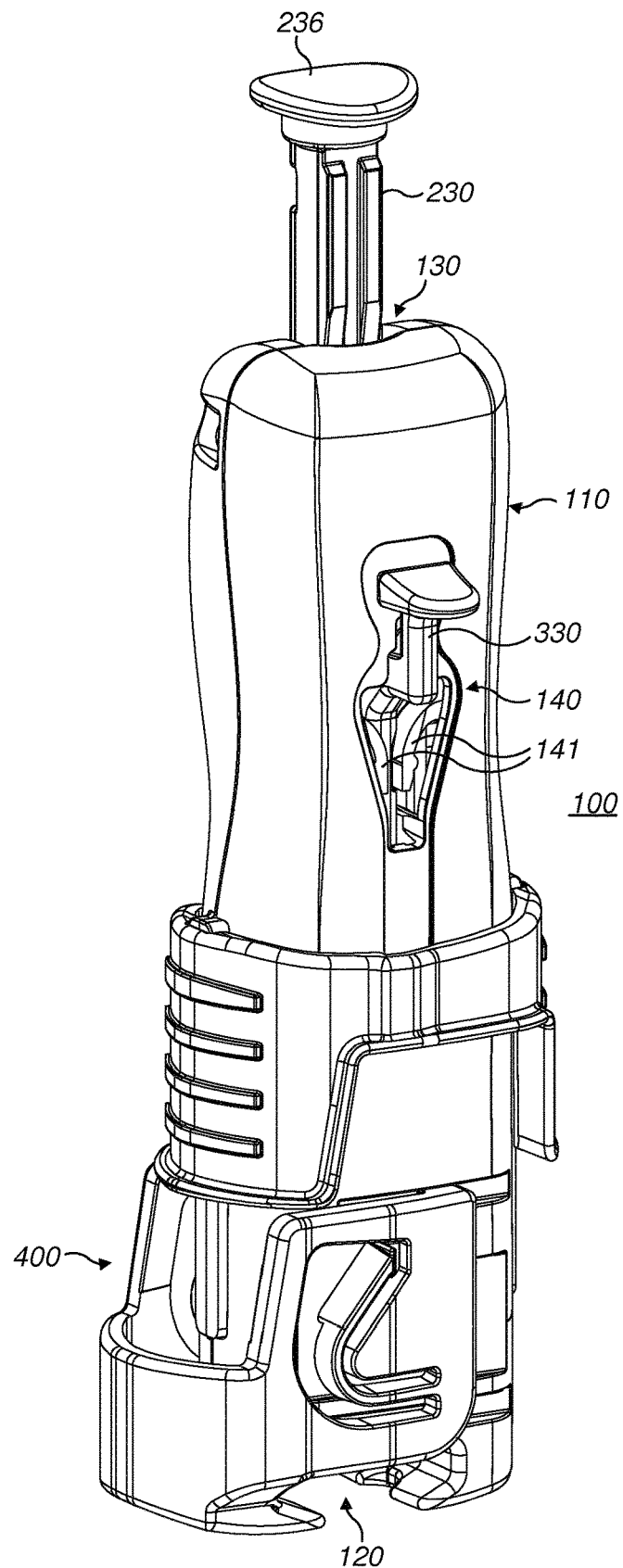
FIG. 1 shows a front view of a tool according to an embodiment.
Figure 2:
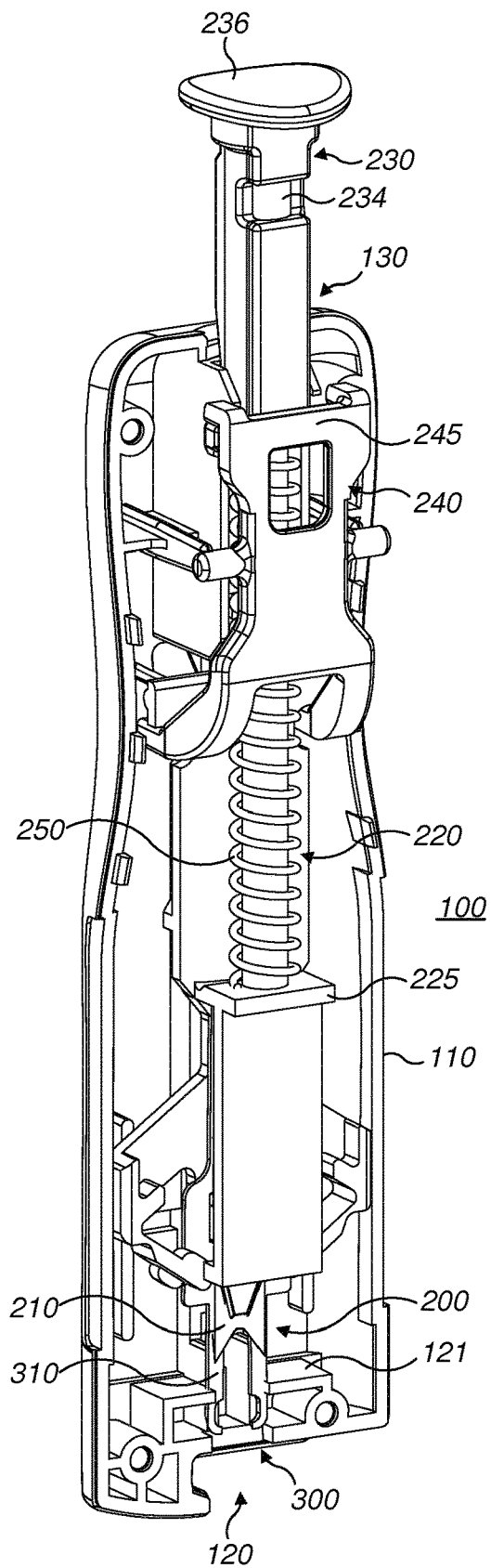
FIG. 2 shows a back view of a tool according to the embodiment with the back housing portion removed to expose the internal components.
Figure 3:
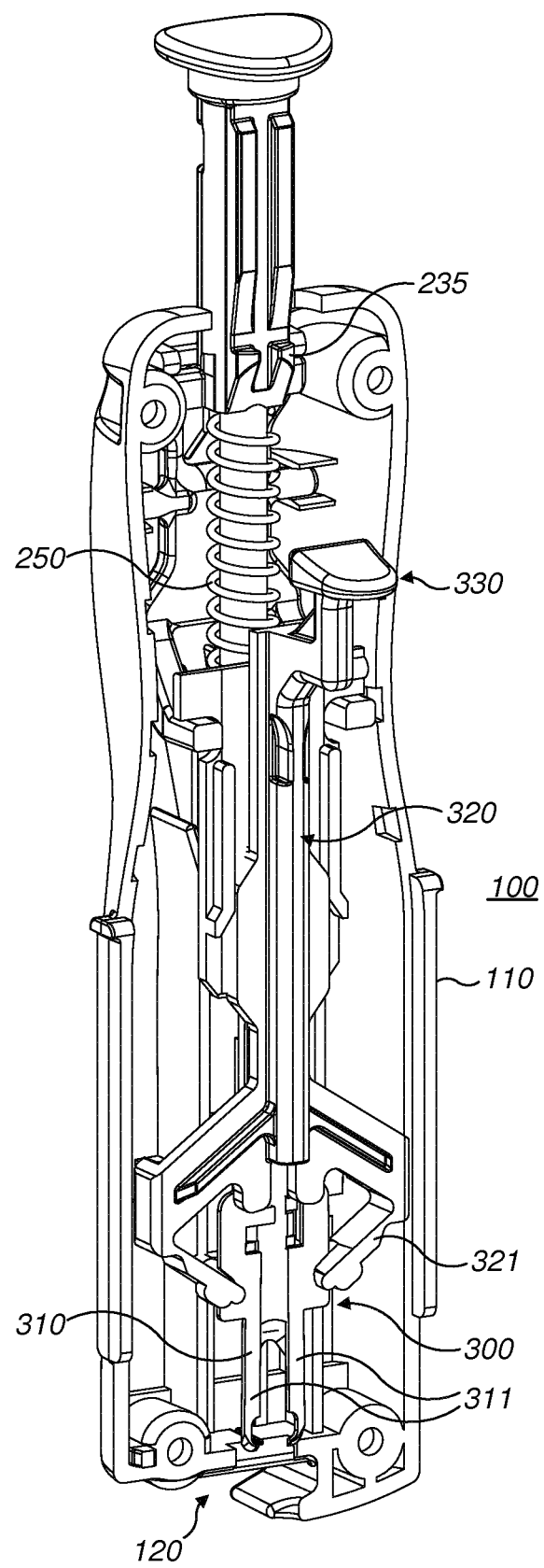
FIG. 3 shows a front view of a tool according to the embodiment with the front housing portion removed to expose internal components.

FIGS. 1 to 3 show a tool according to an embodiment of the present invention. The tool comprises at least a cutting device 200 and a gripping device 300. In the embodiment of FIG. 1 the cutting device 200 and gripping device 300 are disposed within a housing 110 in a first, retracted position before use, with a clamping device 400 provided at a first end of the housing 110. In this embodiment the housing 110 is an elongate shape, defining a long axis at one end of which is a first opening 120 in the housing through which the cutting device 200 and gripping device 300 are moved during use, as will be described.

A first actuating means in the form of a first handle 230 is preferably provided to control the movement of the cutting device 200, the first handle 230 being in mechanical communication with the cutting device 200 within the housing 110 and extending through a second opening 130 at a second end of the housing 110 such that the user may control movement of the cutting device 200 via movement of the first handle 230, as will be described.

A second actuating means in the form of a second handle 330 is similarly provided to control the motion of the gripping device 300. The second handle 330 is connected to the gripping device 300 within the housing 110 and extends through a third opening 140 along an elongate side of the housing 110 such that a user may control movement of the gripping means via movement of the second handle 330.

FIG. 2 shows the tool of FIG. 1 from a view with a side portion of the housing 110 removed so as to expose the internal components of the tool. It can be seen that, in a first, retracted position, the cutting device 200 lies wholly within the tool housing 110. The cutting device 200 of this embodiment comprises a two-pointed, substantially V-shaped blade 210 in mechanical communication with one end of a rod member 220. The blade 210, the rod 220 and the first handle 230 are in mechanical communication and aligned along the long axis of the tool 100 with the points of the V-shaped blade 210 facing the opening 120 at the first end of the housing 110. These components are preferably configured such that, in the first, retracted position shown in FIG. 2 the blade 210 lies within the tool housing 110 and the handle 203 extends from an opening 130 at the second end. A movement regulator component 240 is provided within the tool housing 110 such that the cutting device 200 is secured in this arrangement until a user provides the required action to the application pad 236 of the first handle 230 to move the cutting device 200 from the first position to the second position, in which the blade 210 extends through the first opening 120 in the housing.

FIG. 2 also illustrates the arrangement of the gripping device 300 in a first, retracted position in this exemplary embodiment of the tool according to the invention. In this embodiment the gripping device comprises a tweezer member 310, comprising two parallel gripping arms 311, lying along the long axis of the tool housing, adjacent to the blade 210 of the cutting device 200. In the first position of the gripping device 300, the gripping arms 311 lie in an open position facing the first opening 120 in the tool housing at the first end.

FIG. 3 shows the above described tool according to an embodiment of the invention from the view of FIG. 1 with the side portion of the housing 110 removed so as to show the internal components of the tool. In this view the arrangement of the gripping device 300 is more clearly visible, with the extended, parallel gripping arms 311 of the tweezer device 310 aligned along the long axis of the tool 100. In this first position of the gripping device the curved gripping ends of the tweezer member arms 311 lie just within the first opening 120 of the tool housing 110. The tweezer member 310 is in mechanical communication with a second rod member 320, similarly aligned along the long axis of the tool. The gripping device rod member 320 is connected to the second handle 330, which extends normal to the long axis through the third opening 140 in the side of the housing 110. This arrangement allows a movement of the tweezer member through the first opening 120 in the first end of the housing via movement of the second handle 330 in a corresponding direction. The second rod member 320 further comprises angled locking arms 321, shown in FIG. 3 for holding the gripping arms 311 of the tweezer member 310 in the closed position upon movement out of the first opening 120 of the tool to the second position.

The components of the device are described in more detail below before the process of the operation of the device is outlined.

The Cutting Device

Figure 4A:
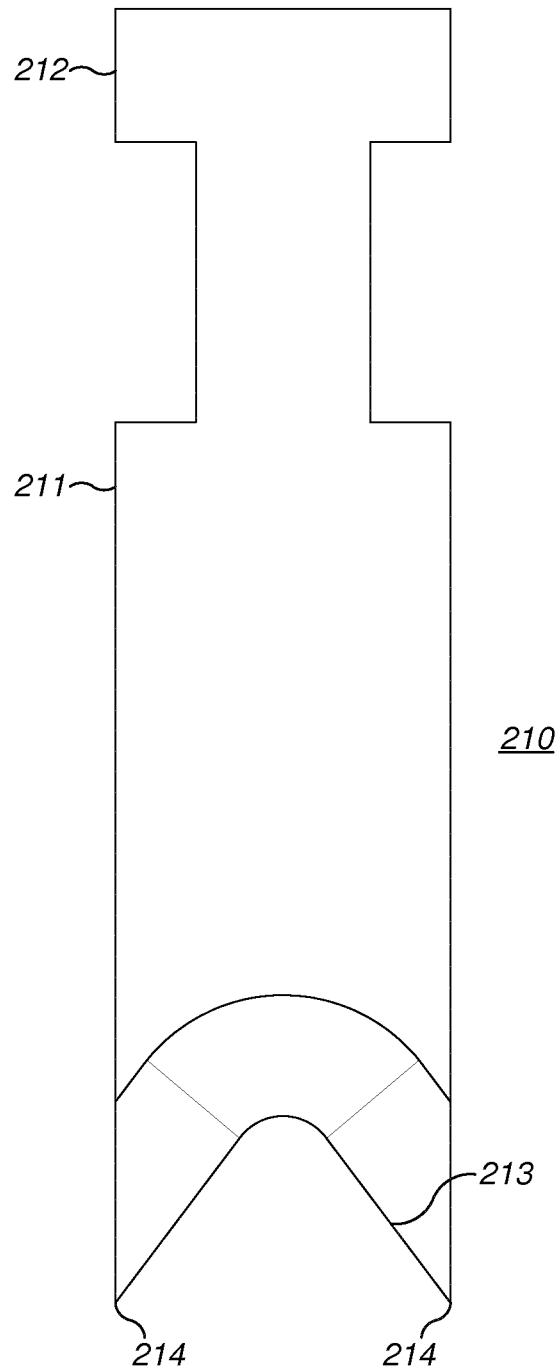
FIGS. 4A and 4B show a front and side view of a blade according to an embodiment.
Figure 4B:
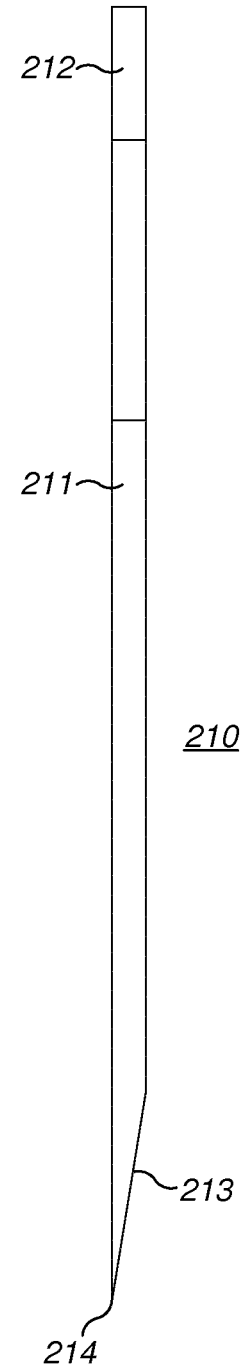

FIGS. 4A and 4B show a possible cutting device according to the present invention. In this embodiment the cutting device 200 comprises an integrally formed twin scalpel blade 210 with an elongate blade body 211 and a T-shaped end portion 212 at the opposing end to the cutting surfaces 213. This T-shaped end portion is configured to interface with the first rod 220, providing a robust mechanical connection through the rod 220 to the handle 230. The twin scalpel blade of this example comprises two coplanar pointed-tipped blades 213, the tips 214 extending an equal distance in the direction of the long axis of the cutting device. The tips 214 are each formed by an outer straight edge which is continuous with an outer edge of the blade body 211 and an angled inner-facing cutting edge. The angled cutting edges form an acute angle with the straight outer edges and oppose each other, meeting centrally via a rounded edge intersection to form a continuous, approximately V-shaped cutting edge 213. The blade tips 214 preferably have a lateral separation which is greater than the diameter of the rod-shaped implant such that they may pass either side of the implant when entering the skin. In this way, the continuing movement of the V-shaped blade into the skin causes the angled cutting edges to extend the initial incisions made by the blade tips towards each other to produce the final incision of a length corresponding to the tip separation.

FIG. 4B shows the side profile of the cutting device of the above described embodiment. This diagram shows the angle of the cutting edge 213 of the blade 210 in the direction normal to the plane of the flattened blade body 211. Preferably this is a very acute angle to provide a sharp cutting edge and therefore increase the ease at which the blade moves through the skin, reducing damage to the surrounding tissue. FIG. 4B also illustrates the thickness of the blade, in this embodiment around 0.5 mm, which defines the width of the incision wound produced in the skin.

Figure 5A:
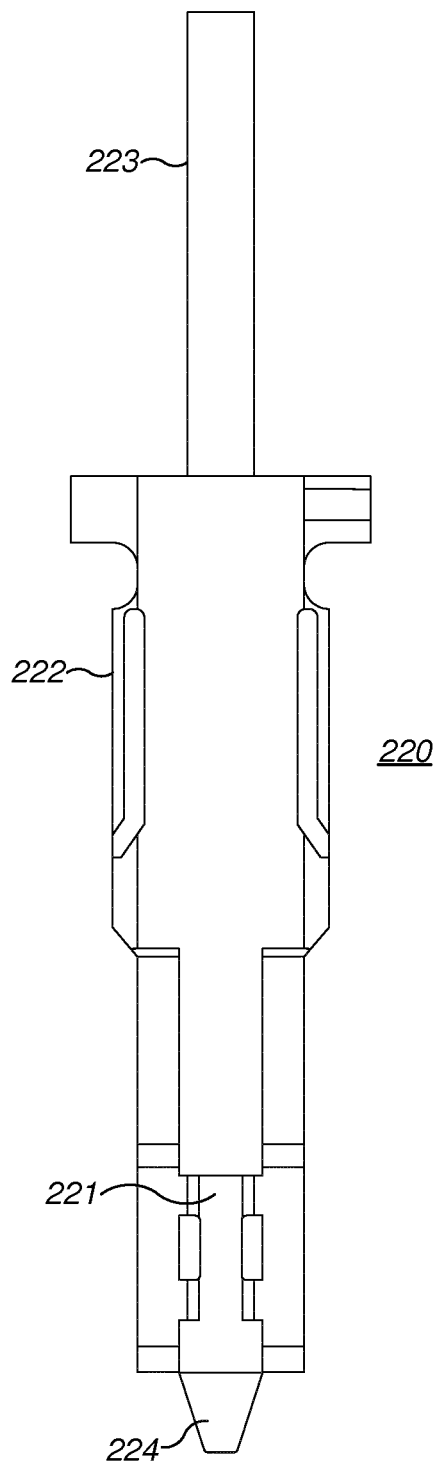
FIGS. 5A and 5B show a front and side view of a control rod of the cutting device according to an embodiment.

FIG. 5A shows a rear view of the first rod member 220 according to an embodiment of the present invention. The rod member has an elongated shape configured to align along the long axis of the tool within the housing 110 with a first end facing the first opening 120 at the base of the housing. A recessed T-shaped depression 221 is provided at this first end, configured to accept and support the T-shaped blade body 211, 212 of FIG. 4A. This allows for the blade to be attached to the first end of the rod member 220 and aligned along its elongate axis such that movement of the rod member 220 produces a corresponding movement of the blade 200. The rod member 220 may further comprise a flat T-shaped body portion 222 and extended cylindrical shaft 223, both extending parallel to each other along the long axis of the rod 220. The cylindrical shaft is configured to support a trigger spring 250, coiled around its diameter and extending along its length. A first end of the trigger spring 250 rests against a ledge 225 which lies normal to the axis of the shaft 223 at a first end.

Figure 5B:
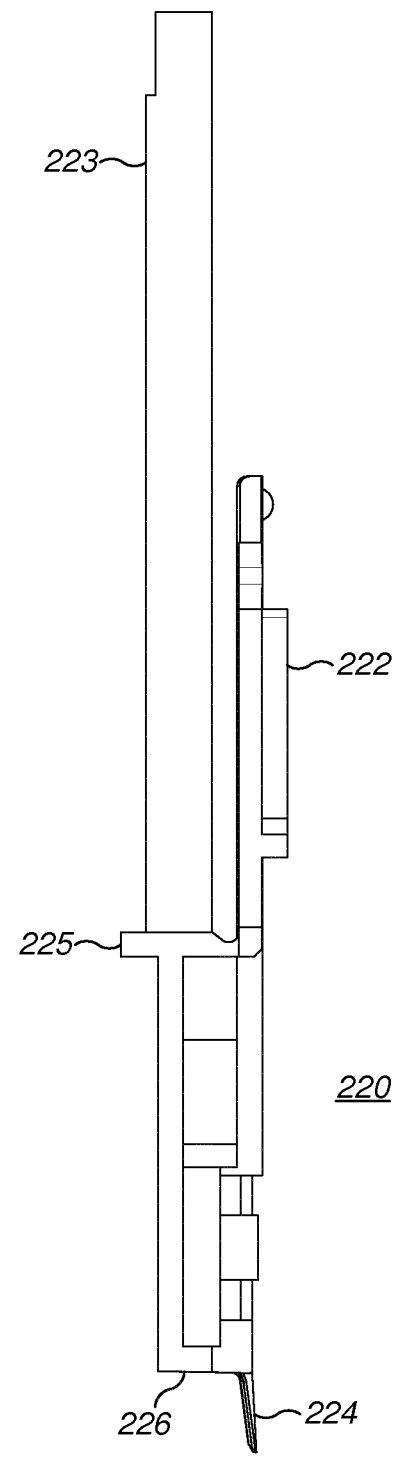

At the first end of the rod member there is further provided a blunt protrusion 224, extending in a direction according to the elongate axis of the rod member 220. As may be seen in FIG. 5B, the protrusion 224 is flat and extends within the plane aligned with the surface of the T-shaped recess 221 such that the blade lies against the protrusion 224 when engaged in the recess. The protrusion may be of appropriate length such that it extends to close to the base of the V-shaped blades when the blade is secured on the rod, as may be seen in FIG. 2. In this arrangement, a blunt front surface of the protrusion restricts the cutting of an implanted item during use since, after a certain degree of travel of the blade, the front surface of the protrusion 224 will make contact with the implant preventing the sharp edge of the blade travelling further into the implant.

Figure 6A:
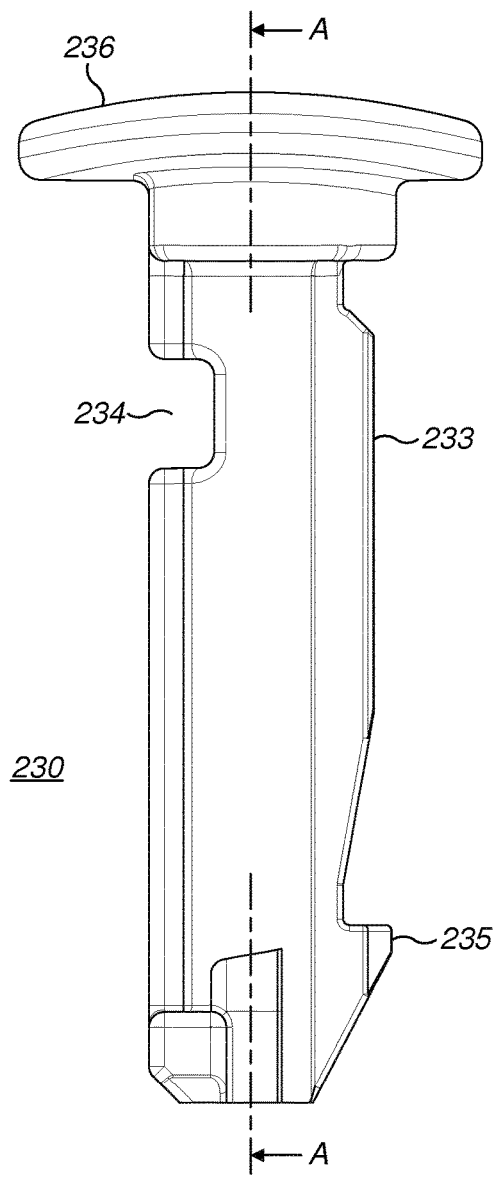
FIGS. 6A and 6B show a side view and front cross section of a first handle according to an embodiment.
Figure 6B:
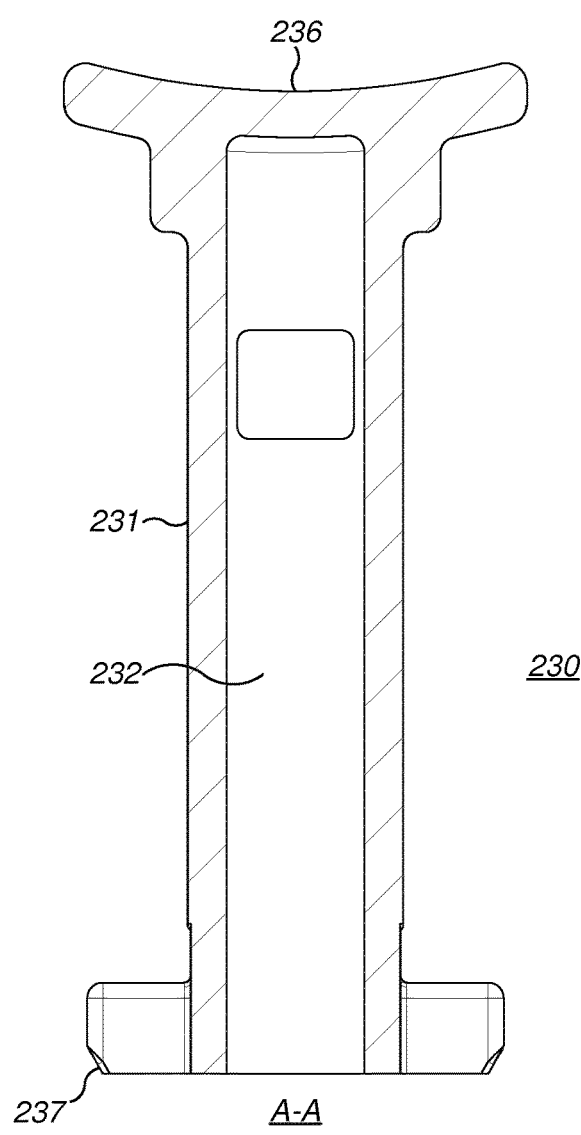

FIGS. 6A and 6B show a side view and a front cross section through a first handle member 230 according to an embodiment of the present invention. The first handle member comprises a substantially hollow, elongate body 231 as illustrated in the cross section of FIG. 6B. The dimensions of the inner hollow chamber 232 of the handle body are chosen such that the shaft 223 of the cutting device rod 220 fits closely inside, providing the required mechanical communication between the handle 230 and rod 220. The handle further comprises protrusions 237 at the first, rod-facing end. The trigger spring 250 has a diameter larger than that of the hollow chamber 232 but less than that defined by the protrusions 237 such when the trigger spring is installed on the shaft 223 of the rod and the handle 230 mounted on the shaft 223, the trigger spring is confined along the axis of the shaft between the ledge 225 of the rod 220 and the protrusions 237 of the handle 230.

FIG. 6A further illustrates the profile shape of the front surface 233 of the handle which has an inclined wedge shape to provide a trigger mechanism as will be described. A wedge shaped protrusion 235 is further provided at the first end of the front face of the handle 230. The wedge shaped protrusion 235 is configured such that, in the first position of the cutting device 200, it sits just within the second opening 130 of the tool housing 110, as is clear in the diagram of FIG. 3. On the opposite side of the wedge shaped protrusion 235 to the angled face is a flat face which lies normal to the long axis of the tool when the handle 203 is installed, lying along the axis of the tool 100. The upwards movement of the handle through the second opening 130 of the tool housing (the direction opposite to the movement from the first to second position in the cutting action) is therefore limited by the flat surface contacting an edge of the tool housing around the second opening 130. This arrangement may therefore prevent removal of the handle 230 through the second opening 130 at the top of the tool housing 110.

FIGS. 7A and 7B illustrate a possible form of a movement regulator 240 of the cutting device 200 of an embodiment of the invention. The cutting device movement regulator 240 occupies a position within the tool housing 110 near the second opening 130, as shown in the rear view of FIG. 2. The regulator 240 may comprise a substantially flat body portion 241 which, in a first position, lies in a plane parallel with the front and rear surfaces of the tool housing 110, displaced to one side of the internal space of the housing 110, leaving a majority of the cross sectional area of the tool housing free for the rod member 220. It is pivotally attached to the inside of the tool housing via two arm members 242 extending from a central position in the plane of the body 241. The arm members 242 define an axis about which the movement regulator 240 may rotate anticlockwise within the housing from the first position, shown in FIG. 2, to a second position. As illustrated in FIG. 7B, two leg members extend from a lower side of the regulator, as arranged within the tool. The leg members 243 curve out of the plane of the body 241 into a plane substantially normal to this, extending across an internal cross section of the tool housing 110 to approach the front face of the tool housing. The two leg members 243, the body of the regulator and the front face of the tool housing therefore define an aperture, through which the shaft 223 of the rod may pass, as shown in FIG. 2.

The cutting device movement regulator 240 further comprises a window 244 in the body portion 241. Most clearly shown in FIG. 2, the top side of the window and top surface of the regulator define a bar shaped portion 245 which is configured to engage with a similarly shaped recess 234 in the handle upon movement of the handle 203 from the first to the second position. Since the rear surface of the handle 230 has a wedge shaped profile of increasing thickness from the first end to the second end, movement of the handle 230 into the device from the first to the second position causes an increasing biasing force of the rear surface of the handle against the regulator 240 as the rear surface slides past the inner surface of the regulator. Therefore, when continued downward movement brings the top bar portion 245 of the regulator into contact with a recess 234 of the handle, the top bar portion drops into the recess causing the movement regulator to rotate anticlockwise out of the first position, shown in FIG. 2, into a second position in which the leg members 243 are moved out of the path of the T-shaped top portion 222 of the rod, allowing the cutting device to be released.

The arrangement and movement of these components of the cutting device 200 may be summarised as follows. Firstly the blade 200 is secured in the corresponding T-shaped recess 221 at the first end of the rod member 220. The shaft 223 of the rod member 220 is secured within the hollow inner chamber 232 of the handle 230 with the trigger spring 250 mounted around the rod shaft 223, the spring extending from the ledge 225 of the rod to the protrusions 237 at the base of the handle. The spring has a diameter wider than that of the hollow inner chamber of the handle 230 such that it may be compressed by the handle as it moves over the rod shaft 223. The T-shaped top portion 222 of the rod 220 lies against the legs 243 of the movement regulator, the legs 243 preventing any downward movement of the combined rod 220 and blade 210 from the first position towards the second position. Furthermore upwards movement of the components (in a direction opposite to that moved in moving to the second position) is prevented by contact between the flat upper surface of the protrusion 235 of the handle meeting an edge defining the aperture of second opening of the tool housing.

The blade 210, the rod 220 and the handle 230 are therefore substantially secured and aligned along a central long axis of the tool within the housing. These combined components therefore may move along a direction corresponding to this axis from a first position to a second position. In the first position the handle 230 extends from the opening 130 at the second end of the housing 110 and the blade is wholly contained within the tool housing.

A sufficient user applied force to the application pad 236 of the handle 230 therefore moves the handle down over the initially stationary rod shaft 223, the rod being held in place by the legs 243 of the movement regulator 240. This action compresses the trigger spring 250 between the ledge 225 of the rod 220 and the protrusions 237 of the handle 230. Continued movement of the handle over the shaft 223 into the second opening of the housing brings the handle notch 234 into alignment with the top bar portion 245 of the trigger member. At this point the movement regulator 240 rotates out of its first position, the top bar portion 245 dropping into the notch 234 in the handle and the legs 243 of the regulator 240 rotating out from underneath the T-shaped top portion 222 of the rod 230.

Since the trigger spring 250 applies a downward force to the cutting device rod 220 via the ledge 225, when the rod is no longer supported by the legs 243 the combined rod 220 and blade 210 are accelerated downwards from the first position towards the second position. The blade 210 of the cutting device 200 therefore moves such that the cutting surfaces 213 of the blade 210 extend through the first opening 120 of the tool housing into the second position.

The exemplary embodiment described above provides one possibility in which the trigger mechanism for the cutting device may be implemented but various alternative implementations also fall within the scope of the invention. In one such alternative, the recess 234 in the handle is configured to engage with a part of the tool housing rather than bar shaped portion 245. In this implementation, the first position of the rod 220 is the same as the previous example. That is, the arms of T-shaped portion 222 on the first rod member 220 are hinged on top of the protrusions 243 of the movement regulator 240. In the resting position, this prohibits downward movement of the first rod member. Similarly, the top protrusions of the movement regulator 240 (shown extending perpendicularly at the top of the component in FIG. 7B) are hinged on top of the protrusions 237 of the first handle member 230.

As the first handle member is manually pressed downwards, the recess 234 of the handle member 230 reaches the tool housing. The recess 234 allows the slight movement of the first handle member towards the back of the device. The result of the slight movement is that the protrusions 237 of the first handle member 230 and the top protrusions of the movement regulator 240 unhinge, and the movement regulator 240 rotates slightly clockwise as it is unhinged. This again causes the legs 243 of the movement regulator 240 to displace backwards, and for them to unhinge from the arms of the T-shaped top portion 222 of the first rod member 220.

As the spring 250 was compressed during the manual downwards movement of the first handle member 230, the stored energy from the spring causes the first rod member 220 to move downwards to a second position upon unhinging from the movement regulator 230 as described above.

The Gripping Device

Figure 8A:
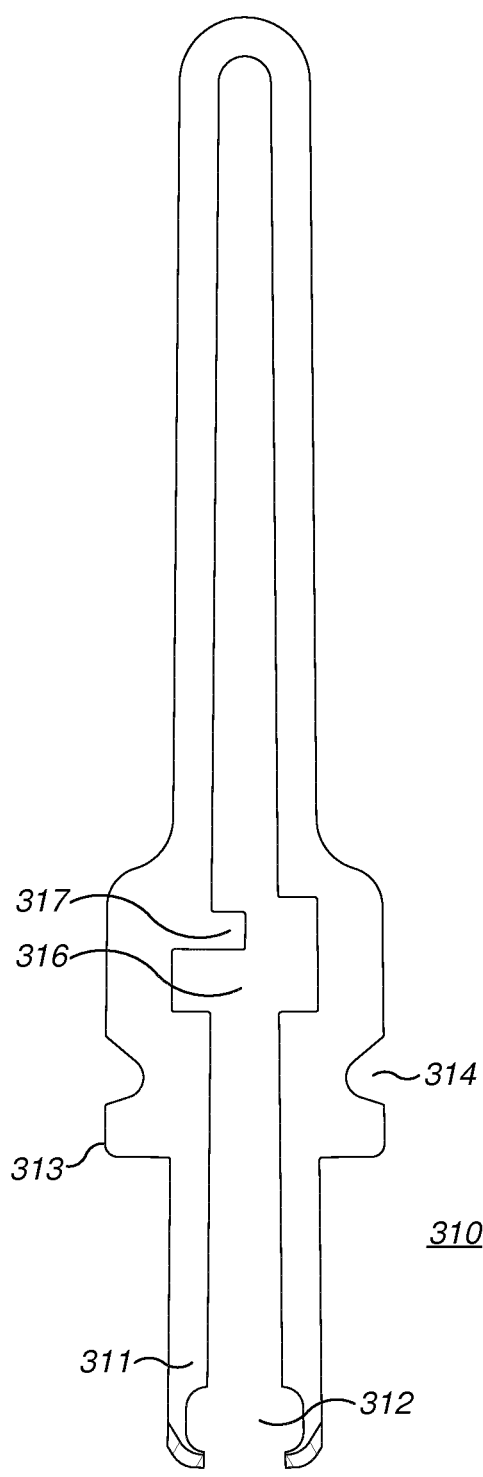
FIGS. 8A and 8B show a font and side view of a tweezer member according to an embodiment.
Figure 8B:
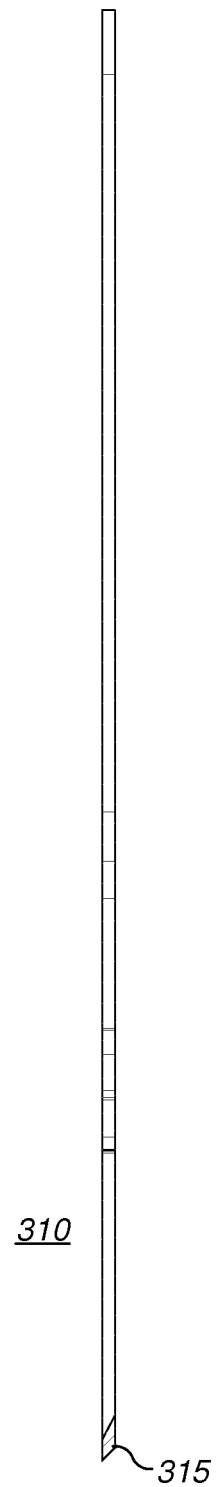

In an embodiment according to the present invention the gripping device 300 comprises a tweezer member 310 as illustrated in FIGS. 8A and 8B. In one example the tweezer member 310 comprises an integral elongated U-shaped unit, the ends of which provide two opposing gripping arms 311. In a first position, prior to use of the tool, the gripping arms lie substantially parallel but an appropriate force applied to the outside of the arms in an inward direction may bring the ends of the arms 311 together into a gripping position. The tips of the arms curve toward one another with a rounded portion of the inside edges cut away so as to define a substantially circular gripping surface 312 created by the engaged gripping arms of the tweezer member. The size of the circular gripping surface 312 may be configured so as to be similar to the cross sectional diameter of a rod shaped implant in order to enhance the gripping function of the device.

Following the inner profile of the arms 311 away from the tips, after the circular gripping surface 312 the inner opposing surfaces of the arms run parallel with a constant separation until, at a certain position along the arms, they open out into a square shaped cutaway 316. On the opposite side of the square shaped cutaway 315 to the tips of the arms there is provided a rectangular protrusion 317 which extends out from the inside edge of one of the arms towards the other. These features are configured to interact with a square shaped protrusion on an inner surface of the housing extending perpendicular to the plane of the grippers, which is configured to regulate the gripping process, as will be described.

As shown in FIG. 8B, the tweezer member is a substantially flat unit which may have a thickness of around 0.5 mm. The extended gripping arms of the tweezer member therefore operate within this plane. FIG. 8B further shows the tips 315 of the gripping arms are angled into a point so as to improve the ease with which they pass into the opening in the skin cut by the cutting device. When arranged in the device the flat surface of the tweezer means lies against that of the blade such that distal movement of the gripping device from a first to second position moves the gripping means along a path closely adjacent to that of the blade 210 such that it may move through the opening in the skin.

The outer edges of the gripping arms, from arm end moving toward the U-end, follow a profile that first has a step in width provided by a flat edge normal to arms 311, a rounded notch 314 is then provided in the section of increased width which then returns via a gradient to the initial thickness of the arms. This profile shape is configured to provide the closing of the gripping arms via interaction with a second rod 320 connected to the gripping means, as will be described.

Figure 9A:
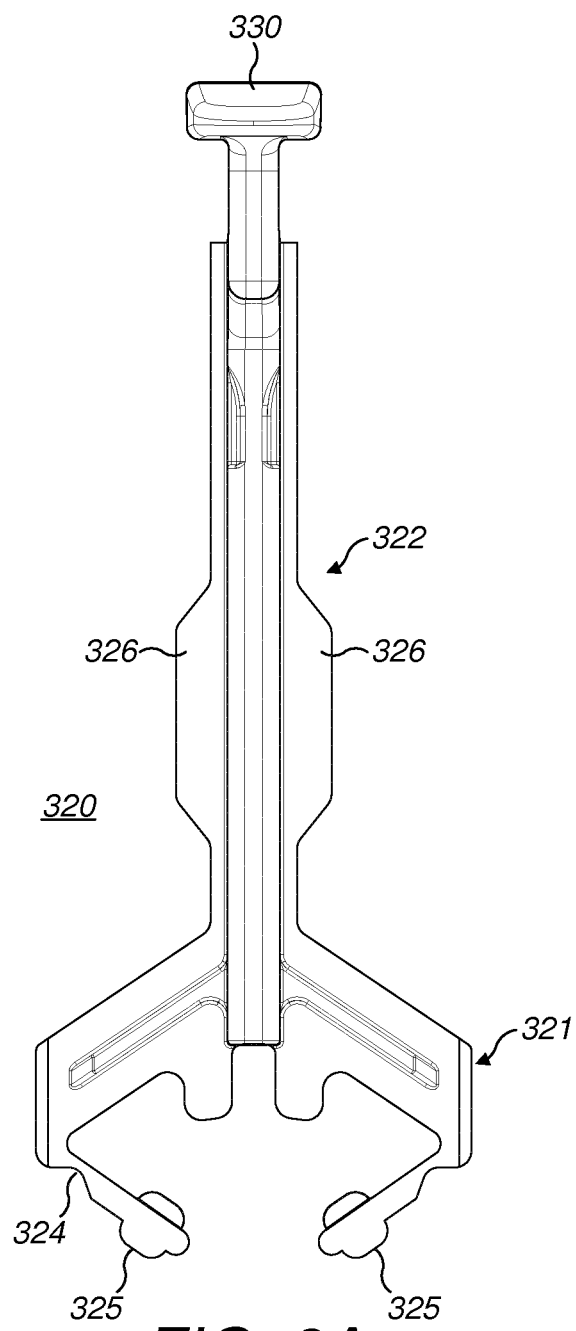
FIGS. 9A and 9B show a front and side view of a control rod of a gripping device according to an embodiment.
Figure 9B:
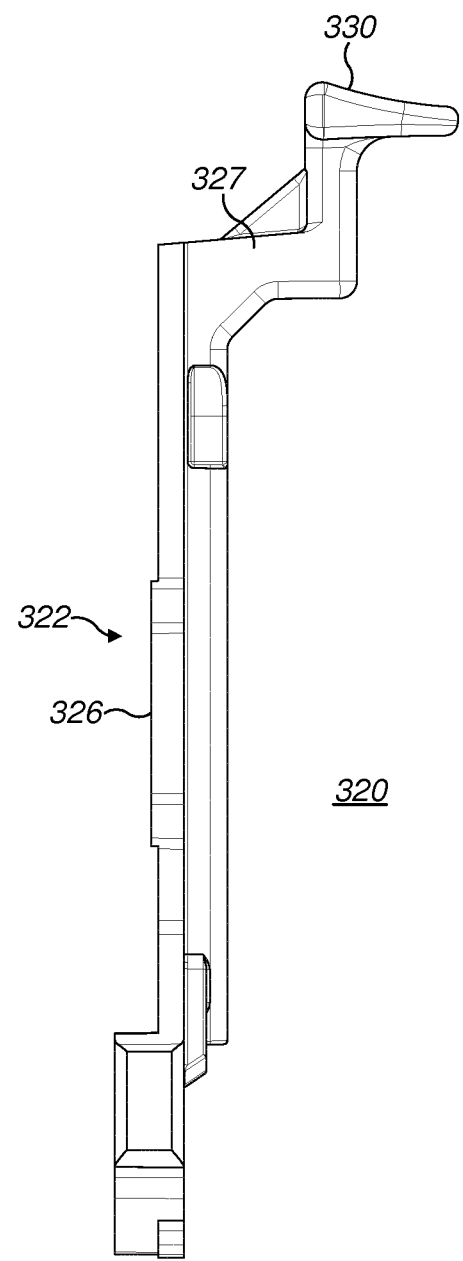

FIGS. 9A and 9B show a control rod 320 of the gripping member 300 of an embodiment, which comprises an elongate body 322 which forks into two angled arms 321 at a first end of the body 322. The angled arms 321 have two main sections; the first extending away from the body angled towards the first end-facing direction, the second section of the arm is angled back in towards the axis of the body 322. A handle 330 is provided at the second end of the elongate body 322 of the control rod 320. The handle 330 extends in a direction normal to the plane defined by the angled arms 321.

The tweezer member 310 is then mounted to the body of the control rod 320 such that they are in mechanical communication and movement of the handle 330 of the control rod results in a corresponding movement of the tweezer member. The mounting may be achieved for example by sliding the tweezer member between two ridges 326 running along either side of the elongate axis of the body 322 of the control rod 320. The tweezer member may be mounted such that it is aligned, parallel against the control rod body 322 with the ends 325 of the inward angled arms 321 resting in the notches 314 on the outward facing edges of the tweezer member. The combined control rod 320 and tweezer member 310 are then mounted within the tool housing 110 such that, in a first retracted position of the gripping device, the tips of the gripping arms are just inside the first opening at the first, i.e. engagement end of the tool. The corners of the angled arms 321 may be mounted in sliders to regulate the movement of the control rod 320 between the first and second position. The handle 330 of the control rod then extends, via a portion 327 perpendicular to the body, through the third opening disposed on the front side of the housing, such that a user may move the combined rod 320 and tweezer member 310 from the first position to a second position in which the curved portion 312 of the gripping arms 311 extends out of the opening at the first end of the housing.

Within the third opening 140 on the inside of the housing 110 there is provided two downwardly protruding members forming a funnel-shaped gate 141. The portion 327 of the control rod handle, which lies normal to the axis of the rod, passes through this gate during movement of the control rod from the first to the second position. The shape of the gate is such that it does not allow movement of the control rod back towards the first position after the portion 237 of the handle has passed through.

In order to provide the required force to the outer edges of the gripping arms to cause them to grip, the angled arms 321 of the control rod 320 may be configured to compress upon the tweezer member 310 reaching its second position. In the first position the ends 325 of the angled arms of the control rod rest inside the notches 314 in the outer edges of the gripping arms 311 of the tweezer member 310. As pressure is applied to the handle 330 and the control rod 320 (and attached tweezer member) is moved downwards towards the first end of the housing, the ledge 313 of the attached tweezer member contacts the surfaces 121 provided either side of the first opening 120, as most clearly visible in FIG. 2. At this point the tweezer member has reached its maximal extension through the first opening and its further progress is prevented by this contact with the inner surfaces 121 of the housing 101. Further pressure on the handle therefore produces a continued movement of the control rod 320 relative to the stationary tweezer member 310. Since the ends 325 of the arms remain stationary along the movement axis within the grooves 314, this continued movement causes the angled arms 321 to increasingly bend at point 324.

The ends 325 of the angled arms 321 therefore provide an increasing force on the outside edges of the gripping arms 311 as the angled arms 324 bend out of their initial downwardly angled position through an orientation in which they are normal with the long axis of the tool and into a final orientation in which they are angled upwards holding the gripping arms 311 of the tweezer member 310 together. In bringing the control rod through the housing of the tool such that the angled arms reach this final holding position, the perpendicular portion of the control rod 327 must pass through the gate 141 in the housing. The control rod is therefore locked in this position since movement back towards the first position is prevented via contact between the handle of the control rod with the protrusions forming the gate 141 and further onward movement out of the first opening 120 of the housing 110 is prevented by contact between the ledge 313 of the tweezer member 310 and inner surfaces 121 of the first opening 120.

The Clamping Device

In an embodiment according to the invention a clamping device 400 may be provided around the first opening 120 in the tool housing 110 at the first end, i.e. engagement end, of the tool 100. The clamping device 400 may be configured to engage with the skin to hold the implanted item in a fixed, known position relative to the tool such that the cutting 200 and gripping devices 300 may be reliably applied to the correct area of the skin in order to remove the implant.

Figure 10A:
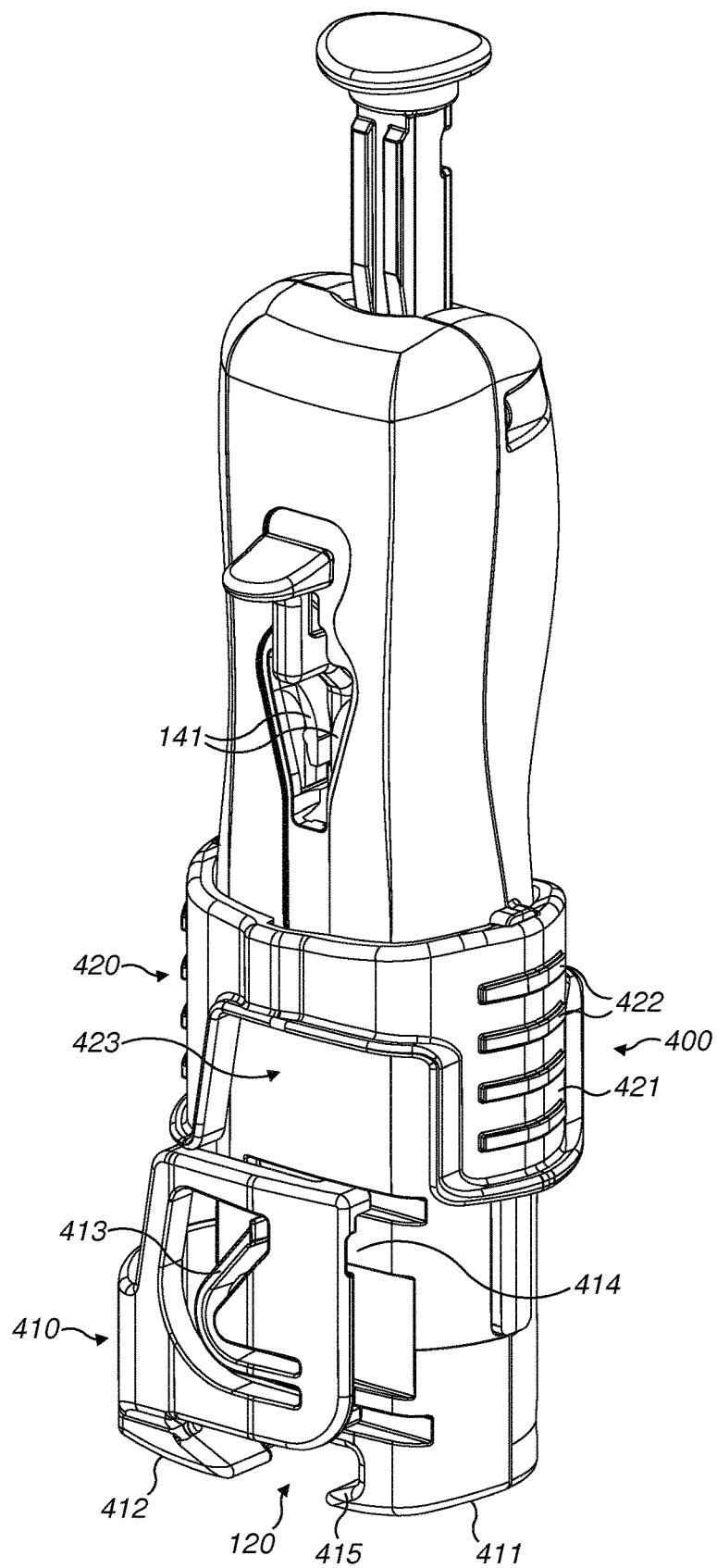
FIGS. 10A and 10B illustrate the operation of a clamping device according to an embodiment.
Figure 10B:
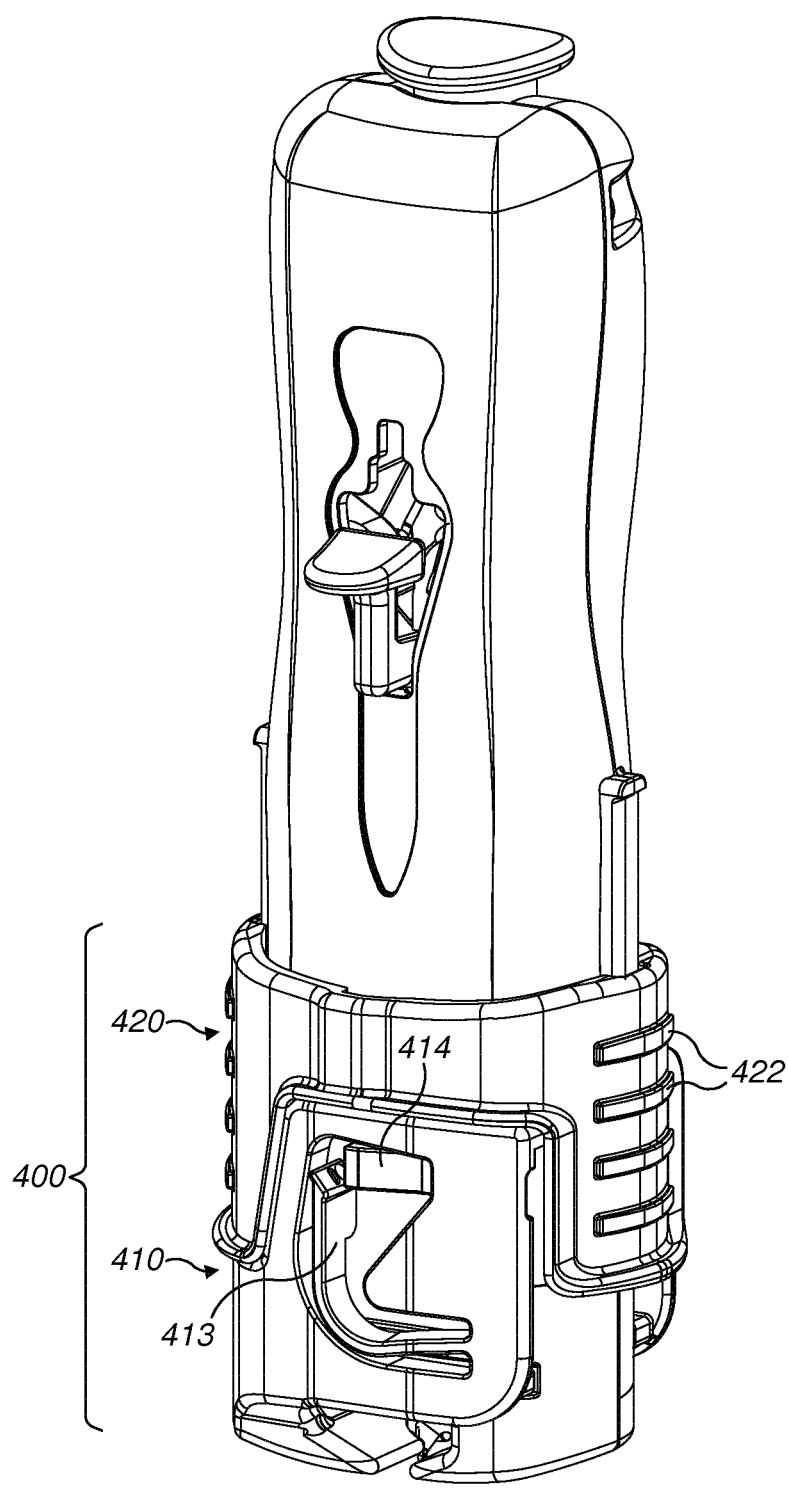

FIGS. 10A and 10B show an exemplary clamping device 400 of the tool according to the present invention. The clamping device comprises two opposing jaws 411, 412 each having an angled pinching surface 415. The jaws 411, 412 are configured to move together around the clamped implant so as to hold it in place beneath the first opening 120 to the housing. One of the jaws 411 is fixed, being integral to the tool housing 110, the second 412 is moveable being disposed on a slideable member 410 such that it may be moved so as to approach the fixed jaw at a position directly adjacent to the first opening 120 in the tool housing 110. The fixed jaw 411 extends from an edge of the tool housing, its pinching surface extending to approximately in line with an edge of the first opening.

The slideable member is mounted to the first end of the tool housing on runners such that the jaws may be moved between an open position and closed position. The runners may be comprised of a protruding ridge 414 running perpendicularly to the long axis of the tool body and a corresponding groove on an inner facing surface of the slideable member 410 such that movement of the slideable member 410 in a direction normal to the axis of the tool is provided. Movement of the slideable member 410 along the protruding ridge 414 in the open direction is limited by a stop positioned in the recess to prevent the further travel of the ridge beyond a predetermined point, maintaining connection between the slideable member and the housing.

Movement of the slideable member 410 to the closed position of the jaws brings the end of an integral torsion spring component 413 into contact with the end surface of the protruding ridge 414 on the outside of the tool housing 110. An additional force in the closure direction therefore has to be applied to overcome the torsion of this component 413 to bring the jaws fully together.

When the jaws 411, 412 are in a substantially closed position, they may be locked in place by moving a moveable sleeve component 420 over the slideable member 410 to hold it in the closed position, as shown in FIG. 10B. The sleeve component 420 is configured to fit closely around the perimeter of the housing and may slide up and down the body in a direction corresponding to the long axis of the tool by provision of protruding ridges along the sides of the housing and corresponding grooves in the inner surfaces of the sleeve component 420. The sleeve component may be formed by two rounded sides 421 which are extended in the long axis direction and provided with gripping ridges 422 to facilitate movement of the component. The front and rear sides of the sleeve component have a cut out portion 423 from the lower edge. This cut out portion fits closely over the slideable member 410, the sides of the extended sides 421 enclosing it so as to releasably hold it in the closed position, as shown in FIG. 10B. When the sleeve components is moved away from the closed jaws, the jaws open and the force provided by the integral torsion spring components 413 which biases the jaws into an open position.

The pinching surfaces 415 of each jaw 411, 412 are wedge shaped so as to partially slide beneath the implanted item within the skin. These angled wedge surfaces 415 act to lift the implanted item up towards the opening at the first end so as to aid in holding it in position and facilitate the extraction of the implant once the incision is made. Furthermore, there is a cut out area provided in corresponding central regions of each pinching surface 415 of the jaws 411, 412 to allow the passage of the tips of the blade 210 which would otherwise contact the jaws when the cutting device 200 is moved to the second position with the clamping device closed.

Operation of the Tool

The implant extraction procedure using the tool will now be described with reference to an embodiment of the tool shown in FIGS. 11A and 11B.

The implanted item is firstly located by touch to initially determine its position under the skin. The jaws 411, 412 of the clamping device are then placed around the implanted item so as to face the elongated sides of the implant. The tool does not need to be aligned precisely centrally to the implant but preferably the two ends of the implant should be observable either side of the clamp jaws 411, 412 to ensure effective lifting of the implant.

Figure 11A:
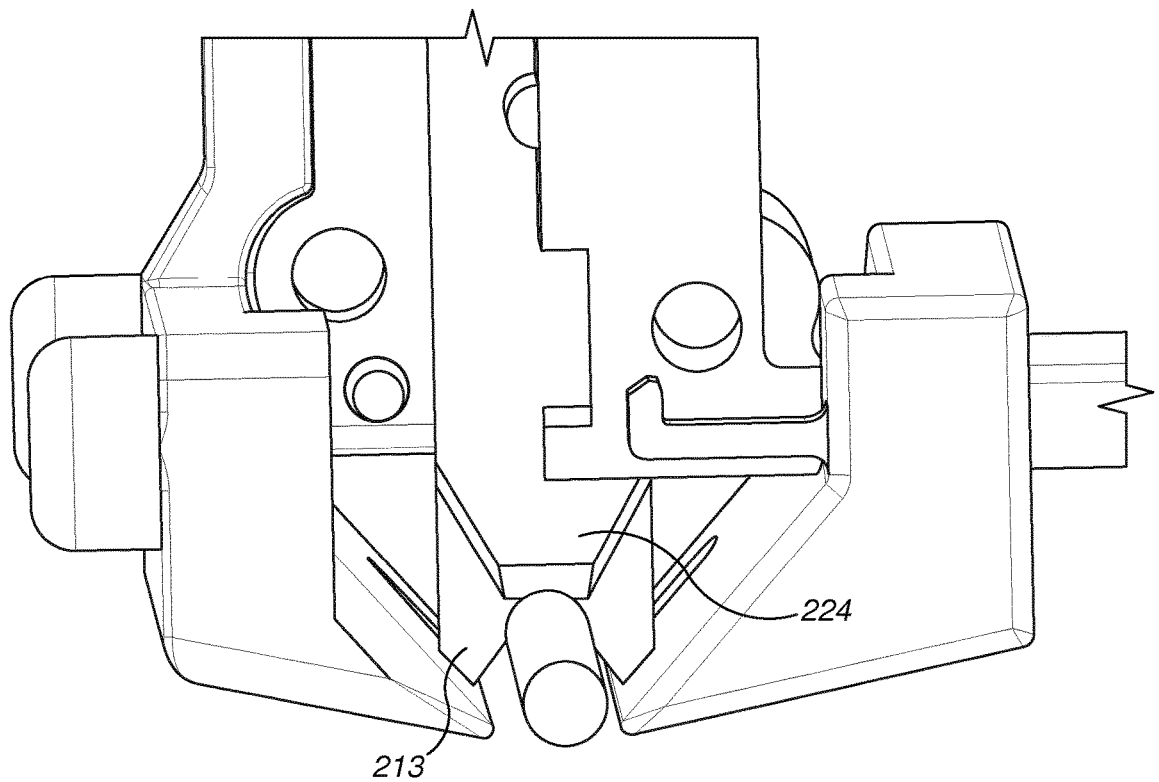
FIGS. 11A and 11B illustrate the implant extraction procedure using a tool according to an embodiment.
Figure 11B:
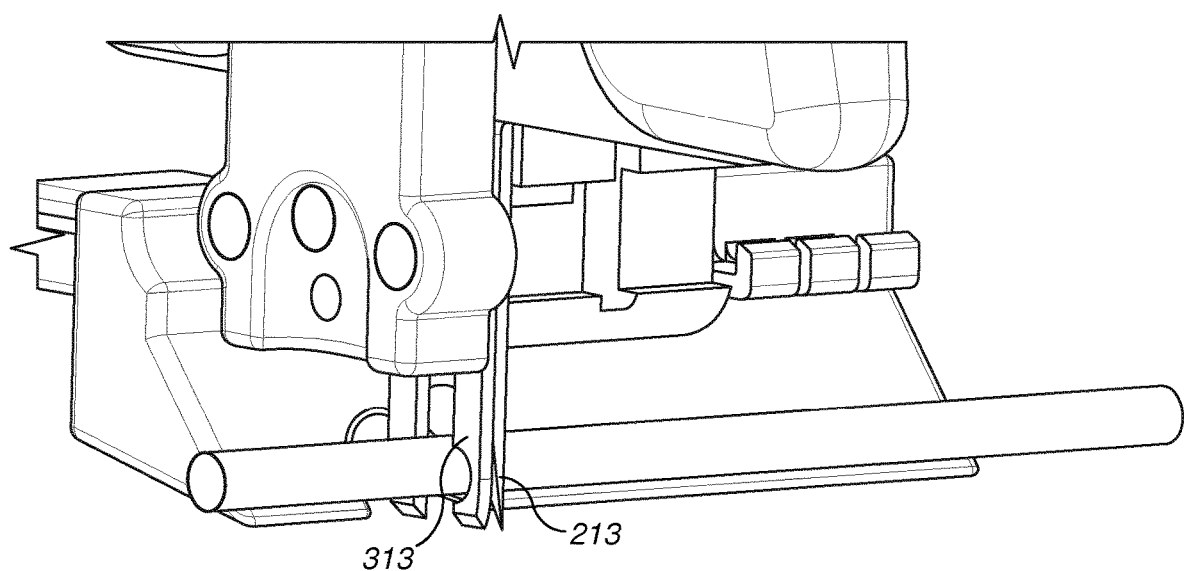

The slideable member is then moved in the closure direction so as to bring the jaw of the slideable member towards the fixed jaw either side of the implanted item, as shown in FIG. 11A. Such a movement encourages the wedge shaped pinching surfaces of the jaws to move partially beneath the implant, lifting it increasingly away from the patient's body beneath the skin as the jaws are moved to the closed position. When the slideable member has reached a closed position in which the implant is sufficiently retained between and above the jaws, the sleeve component is moved down over the slideable member to lock it in place, retaining the implant in a fixed, known position below the opening at the first end of the tool housing, as shown in FIG. 11A.

The user then applies a force to the application pad 236 at the end of the handle 230 of the cutting device 200 in a direction along the long axis of the tool towards the first end. Since the arms 243 of the movement regulator 240 hold the cutting device rod 220 in place, the user applied action to the handle 230 moves the hollow body 232 of the handle down over the stationary rod shaft 220. The trigger spring 250 is then compressed between the ledge 225 of the rod 220 and the handle protrusions 237. When continued movement of the handle brings the notch 234 of the handle 230 into alignment with the top bar portion 245 of the regulator 240, the regulator 240 rotates about the axis defined by the regulator arms 242 such that the regulator legs 243 rotate out from their first position blocking the path of the rod 220 and blade 210. The compressed trigger spring 250 is then released, applying a force to the rod ledge 225 to accelerate the combined rod 220 and blade 210 along the axis of the tool towards the first opening 120. The blade is then moved from its first position within the device along the axis of the tool to emerge from the first opening 120 of the housing. This brings the blade into contact with the skin, the pointed blade tips aligned entering the skin either side of the implant to produce two initial incisions. Continued movement brings the angled cutting edges into the skin, lengthening the incisions towards one another and finally the curved cutting edge interface completes the incision, which has a final length corresponding to the lateral spacing of the blade points.

At this stage, when the cutting device reaches the second position, as shown in FIG. 11A, the base 226 of the body of the cutting device rod 220 contacts the inner surface of the tool housing 110 around the first opening 120, preventing further movement of the cutting device out of the housing 110. Furthermore, the blunt stop 224 of the rod 220, aligned in its position above the cutting edge of the blade, ensures that the blade cannot travel all the way through the implant, as illustrated in FIG. 11A.

The user then applies a force to the handle 330 of the gripping device 300, which causes movement from the first position of the gripping means, in which the tweezer member 310 is contained within the housing 110, in a direction towards the opening at the first end 120. The tweezer member 310, lying against the surface of the blade 210, moves down through this plane and into the incision made by the cutting device 200, as shown in FIG. 11B. The downward movement of the tweezer member is restricted to this second position due to contact between the ledge 313 of the gripping arms 311 with the inner surfaces 121 of the first opening 120 of the housing 110. Continued user-applied pressure on the handle results in continued movement of the control rod 320 relative to the now stationary tweezer member. This movement causes the angled arms to bend upwards since the ends 325 of the arms rest in the notches 314 of the stationary tweezer arms, producing an increasing force on the tweezer arms causing them to grip. As the angled arms 321 of the control rod 320 bend upwards past the normal plane, the portion 327 of the handle passes through the gate 141, preventing the control rod and tweezer means from returning back towards the first position and therefore locking the gripping means closed around the implanted item in the second position.

At this stage the gripping arms 311 are extended into the incision made by the blade 210 with the gripping arms 311 locked around the implant. The final stage of the extraction procedure simply requires releasing of the clamping device 400 by sliding the sleeve 420 component up to release the slideable member 410 and applying force to the housing 110 of the tool 100 such as to pull tool 100 away from the skin, pulling the gripped implant through the opening in the skin made by the cutting device 200. The implant has now been removed from beneath the skin leaving a wound of about 5 mm in size that will typically not require stitches.

The tool according to embodiments of the invention therefore allows for the regulation of the complete contraceptive implant extraction process, radically changing the conventional CI removal procedure. An advantage of use of this tool is that operation does not require any significant user skill, since the main steps are regulated by the features of the tool, yet the procedure has a high reproducibility and high finish quality. The size of incision is highly regulated and damage to the skin and surrounding tissue is minimised. The skill required in successfully finding the implant to directly grip it through the incision is completely removed, with this step in the process regulated by the functionality of the tool. Accordingly, the complete extraction process is standardised and the time taken to complete the procedure significantly reduced. This tool therefore has the potential to facilitate CI removal on a large scale whilst maintaining a high level of finish quality and therefore aids in meeting the forecasted high global demand for CI removal related to the steep increase in CI procurement.

The components of a tool according to an embodiment may have the following approximate dimensions. The body 100 without the handle 230 may be 105 mm long, 30 mm wide and 25 mm thick. The cutting device may be 25 mm long, 5 mm wide and 0.5 mm thick. The gripping device may be 55 mm long, 5 mm wide and 0.5 mm thick.

Figure 12:
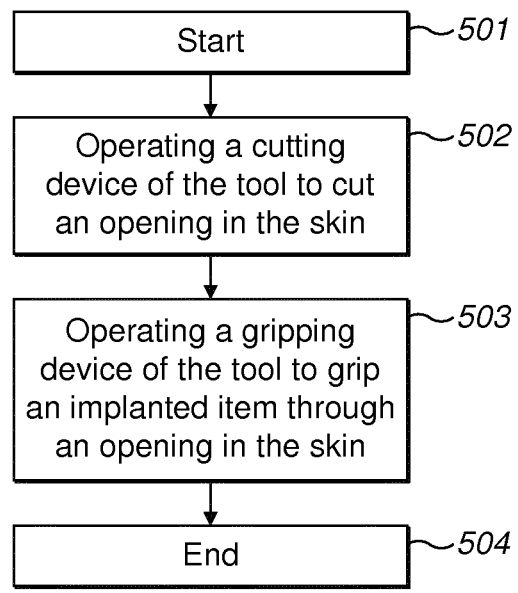
FIG. 12 shows a flowchart of a method according to an embodiment.

FIG. 12 is a flowchart of a method according to an embodiment.

In step 501, the process begins.

In step 502, a cutting device 200 of the tool 100 is operated to cut an opening in the skin.

In step 503, a gripping device 300 of the tool 100 is operated to grip an implanted item through an opening in the skin.

In step 504, the process ends.

Many modifications and variations may be made to the above-described embodiments within the scope of the invention.

Although the tool of the described embodiments comprises a clamp used to hold the implanted item in place, this is not essential and the tool may only comprise the cutting and gripping devices with the tool being held in place by a user. Alternatively, a separate clamping tool may be used to hold the implant in place, for example the tool disclosed in WO 2013/156628.

Although a specific form of the cutting device has been disclosed in which it comprises an integral V-shaped blade, it will be appreciated that many other forms of cutting device may be used within the scope of the claims. For example, the blade may comprise an integral unit with only one cutting surface rather than the opposing V-shaped blade described in relation to the above embodiments.

The cutting device may equally comprise two or more separate blade components. These blade components may for example be overlaid and connected via a pivot to form a scissor-like arrangement.

In a further embodiment, the gripping device is not provided by a separate component, such as the tweezer member of the above described embodiment, rather the gripping device and cutting device may be the same unit. For example, the gripping device may be provided by a notch in one or more of blades of the cutting device wherein the notch is configured to engage with the implanted item as the one or more blades cut through the skin towards the implanted item.

Alternatively, the cutting device may comprise two or more (integral or separate) blades arranged in a scissor-like jaw configuration wherein the gripping device is provided by the gripping action of the blade jaws. In such an arrangement the blades firstly cut through the skin above the implant and subsequently grip the implant between the blade jaws.

Figure 13:
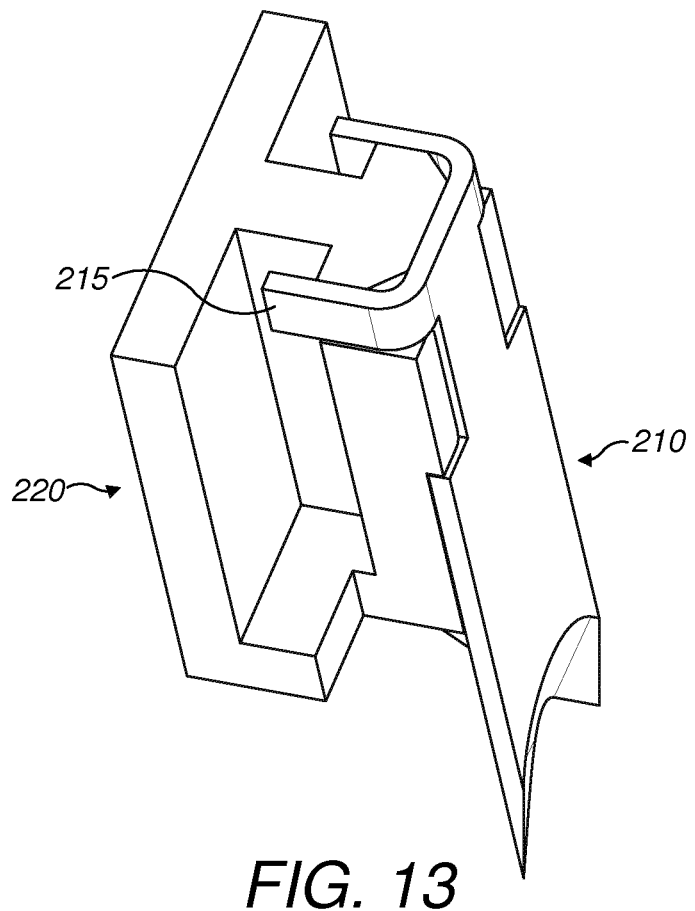
FIG. 13 shows an alternative blade attachment means according to an embodiment.

An alternative means to mount the blade 210 to the first rod member 220 may be used, other than simply providing a recess in the rod of shape corresponding to that of the body of the blade, as outlined in relation to the above-described embodiment. FIG. 13 shows one such alternative in which the arms 215 of the T-shaped end portion of the blade are extended and bend around, out of the plane of the blade into a rear facing direction, normal to the plane of the blade. These extended arms may be configured to wrap around a correspondingly shaped portion of the rod 220 in order to provide an improved mechanical connection between the blade and rod.

In a further variation to the embodiment illustrated in FIG. 13, the blade may have one or more additional pair of arms, spaced away from the first in the direction of the elongate axis of the blade body. By including multiple pairs of arms 215 which bend out of the plane of the blade body, the connection with the corresponding portion of the rod 220 is more stable, reducing the possibility of the blade coming loose. Furthermore, although in FIG. 13 the mounting of the blade with the rod is such that the flat surface of the blade lies against the interfacing portion of the rod and the angled cutting edge 213 of the blade faces away from the rod, the angled cutting edge of the blade may equally face in the opposite direction. In this variation the blade and rod may be adapted such that the legs 215 of the blade bend out of the plane of the blade body on the side having the angled cutting edge, rather than the flat surface of the blade as shown in FIG. 13.

In a further embodiment both of the jaws of the clamping device may move so as to approach and engage the implanted item from both sides during use.

The constituent components of the tool may be assembled in various different ways. In the example illustrated in FIGS. 1 to 3, the opposing housing portions 110 both include circular apertures provided at the four corners of each portion, configured to align when placed together such that the housing portions may be fixed together with screws through these apertures. The circular apertures are clearly illustrated in FIGS. 2 and 3. However in an alternative embodiment, no screws are required but instead the housing portions clip together for example via reciprocal locking features integrally formed with the housing portions. This removes the need for any screws to assemble the device and is therefore advantageous in a reduction of additional, small components which may come loose.

The tool according to embodiments may be configured for a single use only. Preferably, the tool is provided with its cutting and/or gripping devices sterilised and packaged so that the components remain sterile until the device is used.

Alternatively, all parts of the tool may be re-usable. The cutting and/or gripping devices may be re-sterilised and returned to their pre-use positions.

Alternatively, the cutting and/or gripping devices may be single use and the other parts of the tool re-usable. Used cutting and/or gripping devices can be removed and sterile cutting and/or gripping devices can be inserted into the tool.

Alternatively, the cutting and/or gripping devices may be re-usable and the other parts single use. Used cutting and/or gripping devices can be removed and re-sterilized, and assembled with new plastic components.

Preferably the tool comprises a lighting device, such as an LED, and a battery for providing power to the lighting device. The lighting device can indicate to a user if the tool is being operated correctly. For example, it could change colour from red to green when the operator applies sufficient force to release the cutting device so that the operator knows that this part of the procedure has been performed.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

The invention claimed is:

1. A tool for removing an implanted item from beneath the skin, the tool comprising:
   a clamping device configured to engage with the skin to retain the implanted item in a known position relative to the tool, the clamping device including two or more opposing pinching surfaces configured to engage with the skin, wherein the separation between the surfaces can be varied, and the clamping device further including a locking mechanism configured to releasably lock one or more of the pinching surfaces in position at a predetermined separation;
   a cutting device for cutting an opening in the skin; and
   a gripping device configured to move through an opening in the skin and grip an implanted item; such that
   in use, the implanted item is retained by the clamping device substantially in the known position and the cutting device creates an opening in the skin through which the gripping device passes to grip the implanted item.

2. The tool of claim 1 wherein the cutting device is configured to move between:
   a first position, in which the cutting device is retracted within the tool; and
   a second position in which the cutting device extends out of the tool; such that, in use, the movement of the cutting device to the second position brings the cutting device into contact with the skin and cuts an opening in the skin through which the gripping device can pass.

3. The tool of claim 2 further comprising a first actuating means configured to control the movement of the cutting device; such that, in use, when the first actuating means is activated by a user, the cutting device cuts an opening in the skin.

4. The tool of claim 3 wherein the actuating means comprises a first handle and is configured so that, in use, the pressing of the first handle by a user compresses a spring within the housing; and continued pressing of the first handle releases the compressed spring so as to cause the movement of the cutting device.

5. The tool of claim 2 wherein the maximum movement of the cutting device out of the tool is limited by a first stop to the second position.

6. The tool of claim 5 wherein the stop comprises a protrusion on the cutting device configured to contact an element of the tool such that further movement of the cutting device out of the tool is prevented.

7. The tool of claim 1 further comprising a second protrusion on the cutting device, the protrusion configured to contact the implanted item such that, in use, cutting of the implanted item is substantially restricted.

8. The tool of claim 1 wherein the cutting device comprises one or more blades.

9. The tool of claim 8 wherein the cutting device comprises two or more blades, the blades integrally formed as a single unit.

10. The tool of claim 8 wherein the cutting device comprises two or more separate blades.

11. The tool of claim 8 wherein the cutting device comprises two substantially coplanar blades.

12. The tool of claim 11 wherein the lateral separation of the blades is configured such that, in use, parts of the blades enter the skin either side of the implanted item to produce two initial openings.

13. The tool of claim 11 wherein the coplanar blades have equally extending pointed tips and opposing angled cutting edges; wherein the blades are configured such that, in use, the tips enter the skin either side of the implanted item and continued motion of the blades into the skin results in the angled cutting edges extending the initial openings towards one another.

14. The tool of claim 13 wherein the opposing angled cutting edges meet centrally to form a continuous cutting edge.

15. The tool of claim 1 wherein the gripping device is configured to move between a first position and a second position, wherein the second position of the gripping device at least partially coincides with the second position of the cutting device, such that, in use, the gripping device moves through the opening in the skin cut by the cutting device.

16. The tool according to claim 15 wherein the gripping device is configured to move independently to the cutting device.

17. The tool of claim 16 further comprising a second actuating means configured to control the movement of the gripping device, such that, in use, when a user activates the second actuating means, the gripping device moves to the second position of the gripping device, entering the opening in the skin cut by the cutting device and grips the implanted item.

18. The tool of claim 17 wherein the second actuating means comprises a second handle of the tool, the second handle being in mechanical communication with the gripping device such that movement of the second handle causes a corresponding movement of the gripping device.

19. The tool of claim 1 wherein the gripping device comprises a tweezer member, the tweezer member comprising opposing gripping arms configured to grip an implanted item.

20. The tool of claim 19, further comprising a mechanism configured to hold the opposing gripping arms together in a gripping position.

21. The tool of claim 20, wherein the mechanism holds the gripping arms together after the gripping device reaches the second position.

22. The tool of claim 1, wherein the gripping device and cutting device are the same unit.

23. The tool of claim 22 wherein the cutting device comprises one or more blades and the gripping device is provided by a notch in the one or more blades, the notch configured to grip the implanted item such that, movement of the cutting device into the skin, causes the one or more blades to firstly cut an opening in the skin and continued movement brings the notch through the opening into contact with the implant to grip it.

24. The tool of claim 23 wherein the cutting device comprises two or more opposing blades and the gripping device is provided by the gripping action of the two or more opposing blade jaws.

25. The tool of claim 1 wherein at least one of the pinching surfaces forms a wedge shape such that, when the surfaces are brought together in use, the wedge shaped surface moves at least partially below the implanted item to lift it and facilitate the improved retention of the implanted item.

26. The tool of claim 1 further comprising a housing for containing the cutting device and gripping device.

27. The tool of claim 26 wherein the housing comprises:
a hollow body with an opening at a first end, wherein the cutting device and gripping device are configured to move relative to the housing such that they are wholly contained within the body of the housing when in their first positions and extend through the opening at the first end when in their second positions.

28. The tool of claim 27 wherein the clamping device is provided at the first end of the body of the housing, such that, in use, the clamping device engages with the skin and subsequent movement of the cutting device and gripping device to their second positions brings them through the opening in the housing into contact with the skin and the cutting device cuts an opening in the skin through which the gripping device grips the implanted item.

29. The tool of claim 26 wherein the housing is configured to act as a hand grip such that, in use, when the gripping device has gripped the implant, the user may pull the tool away from the skin to extract the implant through the opening in the skin.

30. The tool of claim 1 wherein the tool is configured to be used only once.

31. The tool of claim 1 wherein the cutting device and gripping device are configured to be reset to their first positions after use such that the tool may be used multiple times.

32. The tool of claim 1 wherein selected portions of the tool are configured for multiple use and other portions of the tool are configured for single use.

33. The tool of claim 1 further comprising a lighting device.

34. A method for using a tool to remove an implanted item from beneath the skin comprising the step of:
operating a clamping device of the tool to retain the implanted item in a known position relative to the tool;
operating a cutting device of the tool to cut an opening in the skin; and
operating a gripping device of the tool to grip an implanted item through an opening in the skin.

35. The method of claim 34 further comprising the step of:
operating a hand grip of the tool to pull the tool away from the skin after operating the gripping device such that the implanted item is removed through the opening in the skin.

36. The method of claim 34 wherein the tool comprises
the clamping device configured to engage with the skin to retain the implanted item in the known position relative to the tool;
the cutting device for cutting the opening in the skin; and
the gripping device configured to move through the opening in the skin and grip the implanted item; such that
in use, the implanted item is retained by the clamping device substantially in the known position and the cutting device creates the opening in the skin through which the gripping device passes to grip the implanted item.

\* \* \* \* \*